United States Patent [19]  [11] 4,005,146
Goffinet  [45] Jan. 25, 1977

[54] RESOLUTION OF DL-ALLETHROLONE

[75] Inventor: Bernard Goffinet, Paris, France

[73] Assignee: Roussel-UCLAF, Paris, France

[22] Filed: Sept. 24, 1975

[21] Appl. No.: 616,413

Related U.S. Application Data

[63] Continuation-in-part of Ser. No. 315,999, Dec. 18, 1972, abandoned.

[30] Foreign Application Priority Data

Dec. 28, 1971   France .............................. 71.46981

[52] U.S. Cl. ...................... 260/586 R; 260/DIG. 8
[51] Int. Cl.² ....................................... C07C 45/24
[58] Field of Search ................. 315/999; 260/586 R

[56] References Cited

UNITED STATES PATENTS 3,484,489  12/1969   Krerstead et al. ............. 260/586 R

OTHER PUBLICATIONS

Eliel, "Stereochemistry of Carbon Compounds", pp. 49–55, (1962).
LaForge et al., "J. Org. Chem.", 1970, 26(14), pp. 457–462, (1954).

Primary Examiner—Norman Morgenstern
Attorney, Agent, or Firm—Hammond & Littell

[57] ABSTRACT

A novel process for the resolution of dl-allethrolone or 2-allyl-4-hydroxy-3-methyl-2-cyclopentene-1-one whose chrysanthemic acid esters have insecticidal activity and to novel intermediates.

15 Claims, No Drawings

RESOLUTION OF DL-ALLETHROLONE

PRIOR APPLICATION

This application is a continuation-in-part of my copending, commonly assigned U.S. patent application Ser. No. 315,999 filed Dec. 18, 1972, now abandoned.

STATE OF THE ART

Elliott [J. Sci. Food Agr., Vol. 5 (1954), p. 505] had already indicated that the chrysanthemic acid ester of dextro allethrolone was 4 times more effective as an insecticide than the ester of levo allethrolone, this has been confirmed and comparative insecticidal tests with chrysanthemic acid esters of d-allethrolone and dl-allethrolone are given further on.

LaForge et al [J. Org. Chem., Vol. 19 (1954), p. 457] describes one method of producing d-allethrolone by forming the semicarbazone of dl-allethrolone d-trans chrysanthemate, crystallizing from solution the semicarbazone of d-allethrolone d-trans chrysanthemate, hydrolyzing the crystallized semicarbazone in an alkaline medium to obtain the semicarbazone of d-allethrolone and hydrolyzing the latter with a potassium acid sulfate solution to obtain d-allethrolone.

This method is not useful on an industrial scale because it requires beginning with a very elaborate product, namely dl-allethrolone d-trans chrysanthemate and the yields are mediocre, notably because the resolution is effected with a low yield. Also, the alkaline hydrolysis of the semicarbazone is accompanied with the formation of dimer of allethrolone.

OBJECTS OF THE INVENTION

It is an object of the invention to provide a novel process for the resolution of racemic allethrolone beginning with a simple product and giving good yields without the formation of side products.

It is a further object of the invention to provide novel intermediates for the resolution of racemic allethrolone.

These and other objects and advantages of the invention will become obvious from the following detailed description.

THE INVENTION

The novel process of the invention for the resolution of d,l-allethrolone comprises reacting racemic allethrolone with an excess of a dicarboxylic acid of the formula

HOOC—A—COOH wherein A is selected from the group consisting of alkylene of 1 to 8 carbon atoms and alkenylene of 2 to 8 carbon atoms or a functional derivative thereof to obtain the corresponding ester of the formula

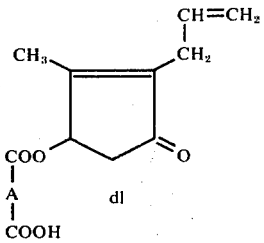

reacting the said ester with an optically active ephedrine in an organic solvent to form the salt of the said base and the said dl allethrolone ester and crystallizing from the organic solvent a salt of the optically active base of the d-allethrolone ester or l-allethrolone ester, reacting the latter with a dilute acid to form the d- or l-allethrolone ester of the dicarboxylic acid and hydrolyzing the latter by heating in an acid media to obtain d- or l-allethrolone.

The dicarboxylic acid preferably has up to 6 carbon atoms and examples of suitable acids are succinic acid and glutaric acid. A suitable functional derivative of the dicarboxylic acid is its anhydride.

The organic solvent for the crystallization of the ephedrine salt of the optically active base may be any appropriate organic solvent in which the said salt is not soluble. Examples of suitable solvents are aromatic hydrocarbons such as xylene, ethylbenzene, styrene, benzene, toluene or mixtures thereof; lower aliphatic alcohols such as isopropanol or tert-amyl alcohol; aliphatic nitriles such as acetonitrile and lower alkyl esters of lower alkanoic acids such as ethyl acetate. The term "lower" is intended to mean 1 to 6 carbon atoms.

The dilute acid that reacts with the ephedrine salt of the hemisuccinate is preferably a mineral acid such as sulfuric acid or hydrochloric acid or an organic acid such as oxalic acid or para-toluensulfonic acid. The hydrolysis with water to obtain the d- or l-allethrolone is effected by heating in an acid media. The acid used preferably for this hydrolysis is sulfuric acid. Acids such as hydrochloric acid, para-toluensulfonic acid, methane sulfonic acids may also be used. The last two steps of the process can be effected in a single step with an acid solution.

The process of the invention is particularly useful for industrial scale because the d- or l-allethrolone ester in the last step is easily provided by hydrolysis without alteration of d- or l-allethrolone. The starting reactants such as succinic anhydride are easily accessible and in another way, the industrial economics of the process are improved by the easy recovery of the optically active base such as ephedrine used in the process. Also, the global yield of the process can reach 80% (as illustrated in the examples) based on the starting material which corresponds to a very large commercial yield.

The process resolves in a satisfactory fashion the known problems involved for the obtention of d-allethrolone and permits for the first time a commercial process for the preparation of d-allethrolone d-trans chrysanthemate which has a much superior insecticidal activity than the corresponding dl-allethrolone ester and it is also possible to obtain l-allethrolone.

The novel intermediate products of the invention are dl-allethrolone esters of formula II, particularly the hemisuccinate of dl-allethrolone; the ephedrine salts of esters of formula II with an optically active base, particularly the ephedrine salts of the hemisuccinate of d,l-allethrolone; and the said salts of the l- or d-allethrolone esters, particularly levo ephedrine salt of the hemisuccinate of l-allethrolone and dextro ephedrine salt of the hemisuccinate of d-allethrolone and the esters of d- or l-allethrolone of the formula

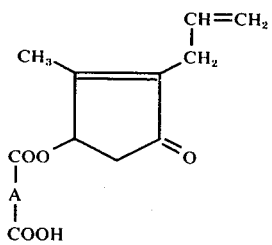

particularly where A is —CH$_2$—CH$_2$—.

In the following examples there are described several preferred embodiments to illustrate the invention. However, it should be understood that the invention is not intended to be limited to the specific embodiments.

EXAMPLE 1

PREPARATION OF d-ALLETHROLONE

STEP A: Hemisuccinate of dl-allethrolone

A mixture of 300 g of racemic allethrolone in 300 ml of pyridine and 300 g of succinic acid anhydride was stirred at 20° C for 48 hours and then 100 ml of water were added thereto to destroy excess succinic acid anhydride. The solution was poured into an aqueous 2N hydrochloric acid solution and the mixture was extracted with benzene. The benzene phase was washed with water, dried and concentrated to dryness by distillation under reduced pressure. The residue was crystallized from isopropyl ether to obtain 381 g of the hemisuccinate of dl-allethrolone melting at 67° C and having an acid no. of 222 (theoretical-222) and a saponification no. of 444 (theoretical-444). A sample after crystallization from isopropyl ether melted at 67° C.

Analysis: C$_{13}$H$_{16}$O$_5$; molecular weight = 252
| Calculated: | %C 61.89 | %H 6.39 |
|---|---|---|
| Found: | 61.7 | 6.2 |

STEP B: dextro-ephedrine salt of hemisuccinate of d-allethrolone 65.5 g of dextro-ephedrine were added at 50° C to a solution of 100 g of the hemisuccinate of dl-allethrolone in 400 ml of ethyl acetate and after stirring for 15 hours at 20° C, the mixture was iced at 0° C for 4 hours with stirring. The mixture was vacuum filtered and the precipitate was washed with ethyl acetate. The precipitate was crystallized from 300 ml of ethyl acetate to obtain 59.6 g of the dextro ephedrine salt of the hemisuccinate of d-allethrolone with a specific rotation $[\alpha]_D^{20} = +34°$ ($c = 5\%$ in water). Crystallization of the product from ethyl acetate gave no change in the specific rotation and the product melted at 106° C.

Analysis: C$_{23}$H$_{31}$O$_6$N; molecular weight = 417.5
| Calculated: | %C 66.17 | %H 7.48 | %N 3.36 |
|---|---|---|---|
| Found: | 66.0 | 7.3 | 3.1 |

The dextro ephedrine salt of the hemisuccinate of l-allethrolone remained in solution in the ethyl acetate.

In an analogous fashion using levo ephedrine in place of dextro ephedrine, levo ephedrine salt of the hemisuccinate of l-allethrolone melting at 106° C and having a specific rotation $[\alpha]_D^{20} = -34°$ C ($c = 5\%$ in water) was obtained while the levo ephedrine salt of the hemisuccinate of d-allethrolone remained in solution in ethyl acetate.

STEP C: Hemisuccinate of d-allethrolone

A solution of 35 ml of an aqueous hydrochloric acid solution of 22° Be in 250 ml of water was added with stirring to a suspension of 150 g of the dextro ephedrine salt of the hemisuccinate of d-allethrolone in 750 ml of benzene at 20° C and after stirring for 1 hour, 2 phases formed. The aqueous phase containing ephedrine hydrochloride was separated by decantation and was reextracted with benzene. The combined benzene extracts were dried and distilled to dryness under reduced pressure. The residue was crystallized from 250 ml of isopropyl ether to obtain 76 g of hemisuccinate of d-allethrolone melting at 66° C and having a specific rotation $[\alpha]_D^{20} = +13°$ ($c = 1\%$ in chloroform).

Analysis: C$_{13}$H$_{16}$O$_5$; molecular weight = 252.26
| Calculated: | %C 61.89 | %H 6.39 |
|---|---|---|
| Found: | 62.0 | 6.2 |

In a similar manner beginning with the levo ephedrine salt of the hemisuccinate of l-allethrolone, the hemisuccinate of l-allethrolone with a specific rotation $[\alpha]_D^{20} = -13°$ ($c = 1\%$ in chloroform) was obtained.

2 g of the hemisuccinate of l-allethrolone were dissolved at 40° C with stirring in 15 ml of isopropyl ether and 1.31 g of dextro ephedrine were dissolved in 10 ml of isopropyl ether. The two solutions were admixed and stirred at 20° C for 12 hours. The mixture was vacuum filtered and the precipitate formed was washed with isopropyl ether and dried at 40° C to obtain 3.2 g of the dextro ephedrine salt of the hemisuccinate of l-allethrolone with a specific rotation $[\alpha]_D^{20} = -1.5°$ ($c = 5\%$ in water).

STEP D: d-allethrolone 65 g of the hemisuccinate of d-allethrolone were added to 325 ml of a 2N hydrochloric acid solution and the suspension was heated at 90° C with stirring for 3 hours. After cooling to 20° C, the solution was saturated with sodium chloride and was extracted with methylene chloride. The extract was dried and distilled to dryness under reduced pressure. The residue was rectified under reduced pressure to obtain 28 g of d-allethrolone with a boiling point of 142° C at 3 mm Hg and a specific rotation $[\alpha]_D^{20} = +15°$ ($c = 1\%$ in chloroform).

Analysis: C$_9$H$_{12}$O$_2$; molecular weight = 152.19
| Calculated: | %C 71.02 | %H 7.95 |
|---|---|---|
| Found: | 70.8 | 8.0 |

U.V. Spectrum (ethanol):
Max. at 230 nm    $E_{1cm}^{1\%} = 806$

-continued

| Circular dichroism (dioxane): | |
|---|---|
| at 346.5 nm | $\Delta\epsilon = +1.30$ (inflexion) |
| at 331 nm | $\Delta\epsilon = +2.89$ |
| at 320 nm | $\Delta\epsilon = +3.18$ |
| at 310 nm | $\Delta\epsilon = +2.43$ (inflexion) |
| at 230 nm | $\Delta\epsilon = -18.72$ |

EXAMPLE 2

Resolution of dl-allethrolone hemisuccinate in toluene

To a solution of dl-allethrolone hemisuccinate obtained from 250 g of dl-allethrolone, 162.5 g of succinic anhydride and 25 ml of methyl ethyl pyridine by a procedure similar to that obtained in Example 1, there were added 1,550 ml of toluene and 252.5 g of d-ephedrine in solution in 775 ml of toluene. The mixture was stirred very slowly for 5 hours and then was allowed to stand for 16 hours. The suspension obtained was then, under very slow agitation, cooled gradually to 0° C and these conditions were maintained for about 20 hours. The precipitate formed was recovered by filtration, was washed and dried to obtain 282.5 g of the dextro ephedrine salt of d-allethrolone hemisuccinate with a specific rotation of $[\alpha]_D^{20} = +32°$ ($c = 5\%$ in water).

EXAMPLE 3

Resolution of dl-allethrolone hemisuccinate in a mixture of toluene and benzene 835 ml of toluene and 165 ml of benzene were added with stirring to the solution of dl-allethrolone hemisuccinate obtained from 150 g of dl-allethrolone, 97.5g of succinic anhydride and 15 ml of methyl ethyl pyridine and then a solution of 152 g of d-ephedrine in 417 ml of toluene and 83 ml of benzene was slowly added. The mixture was stirred slowly for about 6 hours and then was allowed to stand for 16 hours. The suspension was very gradually cooled to 0° C and held at this temperature for 16 hours while stirring slowly. The precipitate formed was recovered by filtration, was washed and dried to obtain 175 g of the dextro ephedrine salt of d-allethrolone hemisuccinate with a specific rotation of $[\alpha]_D^{20} = +32°$ ($c = 5\%$ in water).

EXAMPLE 4

In an analogous manner, l-ephedrine was reacted with dl-allethrolone hemisuccinate to form the levo ephedrine salt of l-allethrolone hemisuccinate which had the same chemical properties as its enantiomer, except for its specific rotation. Various solvents as listed in Table I were used in the resolution and the specific rotation of the said l-ephedrine salt is also listed therein. The $[\alpha]_D^{20}$ for the pure salt is $-34°$

TABLE I

| Resolution solvent | Specific rotation $[\alpha]_D^{20}$ |
|---|---|
| xylene | $-30°$ |
| ethylbenzene | $-24°$ |
| styrene | $-29.5°$ |
| isopropanol | $-27.5°$ |
| tert.-amyl alcohol | $-28°$ |
| acetonitrile | $-27°$ |

EXAMPLE 5

Preparation of d-allethrolone

Steps A and B are effected in an analogous manner as steps A and B of example 1.

Step C: hemisuccinate of d-allethrolone

In a solution of 548 g of dextro ephedrine salt of hemisuccinate of d-allethrolone in 270 ml of aceton was added slowly at 20° C a solution of 92 g of dihydrated oxalic acid in 550 ml of aceton. The reaction mixture was stirred for 16 hours, the precipitate formed was recovered by filtration, washed with aceton and dried to obtain 295 g of dextro ephedrine oxalat. $[\alpha]_D = +34°$ ($c = 0.5\%$, water)/. The filtrate was distilled to dryness under reduced pressure and the crude hemisuccinate of d-allethrolone was obtained.

Step D: d-allethrolone

To the crude hemisuccinate obtained in step C was added under inert atmosphere, 1,200 ml of an aqueous solution of N sulfuric acid which was formerly heated at 90° C. The reaction mixture was stirred at reflux for 3 hours and a half and cooled at + 5° C. The pH was adjusted at 7 by addition of an aqueous concentrate sodium hydroxyde solution. The mixture was saturated with sodium chloride, extracted with methylene chloride. The combined organic phases were dried and charcoal was added. After stirring the mixture was filtered, the filtrate was distilled to dryness, to obtain 176.5 g of d-allethrolone $[\alpha]_D = +11°$ ($c = 10\%$, chloroforme).

INSECTICIDAL STUDY

The lethal insecticidal activity of d-allethrolone chrysanthemate (compound A) was compared with dl-allethrolone chrysanthemate (compound B) on house flies by topically applying 1 $\mu$l of an acetone solution thereof to the dorsal thorax of the insect. 50 insects were used for each dose and the number of dead was determined 24 hours after the treatment. The results are reported in Table II.

TABLE II

| Compound | Dose in mg/l | % Mortality | $DL_{50}$ in mg/l |
|---|---|---|---|
| A | 25 | 49.0 | |
|  | 50 | 45.6 | 54 |
|  | 75 | 76.6 | |
|  | 100 | 65.3 | |
| B | 50 | 16.2 | |
|  | 100 | 33.7 | 224.3 |
|  | 200 | 49.0 | |
|  | 300 | 55.1 | |

The results of Table II show that compound A in this test is 4.15 times more active than compound B.

The knock down effect of the same two compounds was determined on female german cockroaches by direct spraying as 0.5 ml of a solution in equal volumes of kerosene and acetone. 20 insects were used for each test and the knock down effect was determined at 5,10,15,30 and 60 minutes after treatment. The results are reported in Table III.

TABLE III

| Compound | Dose in mg/l | % KD after min. 5 | 10 | 15 | 30 | 60 | KD$_{50}$ in mg/l 5 | 30 |
|---|---|---|---|---|---|---|---|---|
| A | 1000 | 100 | 100 | 100 | 100 | 100 | | |
|  | 500 | 61.9 | 71.4 | 83.3 | 85.7 | 88.0 | 300 | 185 |
|  | 250 | 45.0 | 52.5 | 65.0 | 62.5 | 65.0 | | |
|  | 1000 | 46.1 | 64.1 | 74.3 | 79.4 | 89.7 | | |
| B | 500 | 30.9 | 50.0 | 54.7 | 47.6 | 45.2 | 1300 | 520 |
|  | 250 | 7.5 | 7.5 | 12.5 | 12.5 | 12.5 | | |

The results of Table III show that at a time interval of 5 minutes, the KD$_{50}$ of compound A is about 4.3 times more active than that of compound B and at 30 minutes, the KD$_{50}$ of compound A is 2.8 times more active than that of compound B.

Various modifications of the intermediates and process of the invention may be made without departing from the spirit or scope thereof and it is to be understood that the invention is to be limited only as defined in the appended claims.

I claim:

1. A process for the resolution of dl-allethrolone comprising reacting dl-allethrolone with an excess of succinic acid anhydride to form the hemisuccinate of dl-allethrolone, reacting the latter with ephedrine in an appropriate organic solvent selected from the group consisting of aromatic hydrocarbon, lower alkyl esters of lower alkanoic acids, lower aliphatic nitriles and lower aliphatic alcohols to form the ephedrine salt of the said hemisuccinate and crystallizing from the organic solvent a member selected from the group consisting of dextro ephedrine salt of the hemisuccinate of d-allethrolone and levo ephedrine salt of the hemisuccinate of l-allethrolone, reacting the recovered ephedrine salt with a dilute aqueous acid to form the resulting hemisuccinate and hydrolysing the latter by heating in an aqueous acid media to form the corresponding optical isomer of allethrolone.

2. The method of claim 1 wherein the organic solvent is selected from the group consisting of ethyl acetate, acetonitrile, tert.-amyl alcohol, isopropanol, styrene, ethylbenzene, xylene, benzene and toluene and a mixture of benzene and toluene.

3. The method of claim 1 wherein the solvent is a benzene-toluene mixture.

4. The method of claim 1 wherein the solvent is ethyl acetate.

5. The method of claim 1 wherein the solvent is benzene.

6. The method of claim 1 wherein the solvent is isopropanol.

7. The method of claim 1 wherein the solvent is xylene.

8. The method of claim 1 wherein the solvent is tert.-amyl alcohol.

9. The method of claim 1 wherein the solvent is ethylbenzene.

10. The method of claim 1 wherein the solvent is styrene.

11. The method of claim 1 wherein the solvent is acetonitrile.

12. The method of claim 1 wherein the solvent is toluene.

13. The method of claim 1 wherein the dilute acid that reacts with the ephedrine salt of the hemisuccinate of optically active allethrolone is dilute oxalic acid.

14. The method of claim 1 wherein the dilute acid that reacts with the ephedrine salt of the hemisuccinate of optically active allethrolone is dilute hydrochloric acid.

15. The method of claim 1 wherein the acid in the presence of which the hemisuccinate of optically active allethrolone is heated, is sulfuric acid.

* * * * *